US008163887B2

(12) United States Patent
Hansen

(10) Patent No.: US 8,163,887 B2
(45) Date of Patent: Apr. 24, 2012

(54) USE OF IMMUNOCONJUGATES TO ENHANCE THE EFFICACY OF MULTI-STAGE CASCADE BOOSTING VACCINES

(75) Inventor: Hans J. Hansen, Picayune, MS (US)

(73) Assignee: Immunomedics, Inc., Morris Plains, NJ (US)

(*) Notice: Subject to any disclaimer, the term of this patent is extended or adjusted under 35 U.S.C. 154(b) by 263 days.

(21) Appl. No.: 12/014,547

(22) Filed: Jan. 15, 2008

(65) Prior Publication Data
US 2008/0187515 A1 Aug. 7, 2008

Related U.S. Application Data

(63) Continuation of application No. 08/577,106, filed on Dec. 22, 1995, now Pat. No. 7,354,587, which is a continuation-in-part of application No. 08/268,129, filed on Jul. 6, 1994, now Pat. No. 5,798,100.

(51) Int. Cl.
C07K 16/00 (2006.01)
(52) U.S. Cl. .................. 530/391.7; 530/391.1
(58) Field of Classification Search .......... None
See application file for complete search history.

(56) References Cited

U.S. PATENT DOCUMENTS

| 4,818,709 | A | | 4/1989 | Primus et al. | |
|---|---|---|---|---|---|
| 5,194,254 | A | * | 3/1993 | Barber et al. | 424/178.1 |
| 5,441,871 | A | * | 8/1995 | Seon | 435/7.23 |
| 5,478,556 | A | | 12/1995 | Elliott et al. | |
| 5,530,101 | A | | 6/1996 | Queen et al. | |
| 5,571,515 | A | | 11/1996 | Scott et al. | |
| 5,614,610 | A | | 3/1997 | Hellstrom et al. | |
| 5,798,100 | A | | 8/1998 | Hansen | |
| 5,840,854 | A | * | 11/1998 | Hellstrom et al. | 530/387.7 |
| 5,874,540 | A | | 2/1999 | Hansen et al. | |
| 6,132,718 | A | | 10/2000 | Hansen | |
| 6,440,416 | B1 | | 8/2002 | Hansen et al. | |
| 6,926,893 | B1 | | 8/2005 | Hansen | |
| 7,354,587 | B1 | * | 4/2008 | Hansen | 424/178.1 |

FOREIGN PATENT DOCUMENTS

| EP | 0 306 995 | 3/1989 |
|---|---|---|
| EP | 0324625 A1 | 7/1989 |
| EP | 0 340 793 | 11/1989 |
| EP | 0 438 803 | 7/1991 |
| EP | 0340793 B1 | 8/1995 |
| EP | 0438803 B1 | 3/1997 |
| EP | 0306995 B1 | 4/1997 |
| WO | 91/11465 | 8/1991 |
| WO | 91/11465 A1 | 8/1991 |
| WO | 92/15322 | 9/1992 |
| WO | 92/15322 A1 | 9/1992 |
| WO | 93/11162 | 6/1993 |
| WO | 93/11162 A1 | 6/1993 |
| WO | 93/19163 | 9/1993 |
| WO | 94/05329 | 3/1994 |
| WO | 94/05329 A1 | 3/1994 |
| WO | 96/04313 | 2/1996 |
| WO | 96/04313 A1 | 2/1996 |
| WO | 96/37224 | 11/1996 |
| WO | 96/37224 A1 | 11/1996 |
| WO | 96/40941 | 12/1996 |
| WO | 96/40941 A1 | 12/1996 |

OTHER PUBLICATIONS

Bremnes et al, 1994, J Cell Science, 107: 2021-2031.*
Roche et al, 1993, PNAS, USA, 90: 8581-8585.*
Ikeda et al, 1992, Mol Immunol, 29(2): 229-40.*
Nohria et al, 1994, Biotherapy, 7: 261-269.*
Losman et al, 1994, Intl J Cancer, 56: 580-584.*
Primus et al, 1983, Cancer Res, 43: 686-692.*
William E. Paul, ed., 3rd ed. 1993, Fundamental Immunology, p. 242.*
Palak-Byczkowska et al, 1989, Cancer Res, 49: 4568-4577.*
Hefta et al Cancer Research vol. 52 p. 5647 (1992).*
Carayanniotis, George, et al., "Delivery of Synthetic Peptides by Anti-Class II MHC Monoclonal Antibodies Induces Specific Adjuvant-Free IgG Responses In Vivo" Molecular Immunology, vol. 25, No. 9, pp. 907-911, 1988 XP-000939329.
Nepom, Gerald T., et al., "Induction of Immunity to a Human Tumor Marker by in vivo Administration of Anti-idiotypic Antibodies in Mice," Proc. Natl. Acad. Sci. USA, vol. 81, pp. 2864-2867, May 1984 Immunology XP-002147166.
Losman, Michel J., et al., "Human Response Against NP-4, a mouse Antibody to carcinoembryonic Antigen: Human anti-idiotype Antibodies Mimic an Epitope on the Tumor Antigen" Proc. Natl. Acad. Sci. USA vol. 88, pp. 3421-3425, Apr. 1991 Medical Sciences XP-002147167.
Becker, Susanne, "Interferon-γ Accelerates Immune Proliferation via its Effect on Monocyte HLA-DR Expression" Cellular Immunology, 91, 301-307 (1985) XP-000939351.
Bohlen, Herbert et al., "Idiotype Vaccination Strategies against a murine B-cell lymphoma: Dendritic cells loaded with idiotype and bispecific idiotype X anti-class II antibodies can protect against tumor growth" Cytokines and Molecular Therapy, 1996 vol. 2, pp. 231-238 XP-000946037.
Yu, Zhiwei, et al. "Peptide-Antibody Conjugates for Tumour Therapy: A MHC-Class-II-Restricted Tetanus Toxin Peptide Coupled to an Anti-Ig Light Chain Antibody can induce Cytotoxic Lysis of a Human B-Cell Lymphoma by Specific CD4 T Cells" Int. J. Cancer: 56, 244-248 (1994) XP-000946044.
J. Cohen, "Cancer Vaccines Get a Shot in the Arm", Science, vol. 262, Nov. 1993, pp. 841-843.

(Continued)

Primary Examiner — Sheela J Huff
(74) Attorney, Agent, or Firm — Richard A. Nakashima

(57) ABSTRACT

Humoral and cellular immune responses against tumor cells and infectious agents are induced in a mammal using a vaccine comprising immunoconjugates that comprise antibodies and anti-idiotype antibodies that mimic an epitope of an antigen that is associated with a tumor or an infectious agent. These immunoconjugates also comprise a peptide that contains an epitope of a tumor associated antigen or infectious agent antigen, a peptide that contains a minimal recognition unit of an anti-idiotype antibody, or a peptide that induces a strong major histocompatibility complex-restricted immune response. Antibodies and cytokines also may be used to amplify the immune cascade.

14 Claims, No Drawings

OTHER PUBLICATIONS

F. M. Rosenthal., "Human Tumor Vaccines and Genetic Engineering of Tumors with Cytokine and Histocompatibility Genes to Enhance Immunogenicity", Current Opinion in Oncology, vol. 6, Nov. 1994 pp. 611-615.

K. Y. Tsang., "A Recombinant CEA-Vaccinia Vaccine Induces a CEA-Specific Cytotoxic T-Cell Response in Carcinoma Patients", Proceedings of the American Association for Cancer Research, vol. 36, Mar. 1995, p. 249.

L. G. Durrant., "An Idiotypic Replica of Carcinoembryonic Antigen Inducing Cellular and Humoral Responses Directed Against Human Colorectal Tumors", Int. J. Cancer, vol. 50, Mar. 1992, pp. 811-816.

Becker, et al., "Expression of a Hybrid Immunoglobulin-T Cell Receptor Protein in Transgenic Mice", Cell, 68: 911-921 (Sep. 8, 1989).

Bolhuis et al., "T Cell Targeting in Cancer Therapy", Cancer Immul. Immunother., 34: 1-8 (1991).

Bolhuis et al., "Engineering T Lymphocyte Antigen Specificity", Journal of Cellular Biochemistry, 47: 306-310 (1991).

Eshhar et al., "Chimeric T cell receptor which incorporates the anti-tumour specificity of a monoclonal antibody with the cytolytic activity of T cells: a model system for immunotherapeutical approach", British Journal of Cancer, 62 (Suppl 10): 27-29 (1990).

Eshhar et al., "Specific activation and targeting of cytotoxic lymphocytes through chimeric single chains consisting of antibody-binding domains and the gamma or zeta subunits of the immunoglobulin and T-cell receptors". Proc. Natl. Acad. Sci. USA, 90: 720-724 (Jan. 1993).

Fagerberg et al., "Induction of an immune network cascade in cancer patients treated with monoclonal antibodies", Canc. Immul. Immunother., 37: 264-270 (1993).

Goldenberg et al., "Monoclonal antibodies in cancer detection and therapy", American Journal of Medicine, 94: 297-312 (Mar. 1993).

Goverman et al., "Chimeric immunoglobulin-T cell receptor proteins form functional receptors: Implications for T cell receptor complex formation and activation", Cell, 60: 929-939 (Mar. 23, 1990).

Gross et al., "Expression of immunoglobulin-T-cell receptor chimeric molecules as functional receptors with antibody-type specificity", Proc. Natl. Acad. Sci. USA, 86: 10024-10028 (Dec. 1989).

Gross et al., "Generation of effector T cells expressing chimeric T cell receptor with antibody type-specificity", Transp. Proc., 21: 127-130 (Feb. 1989).

Hansen et al., "Characterization of second-generation monoclonal antibodies against carcinoembryonic antigen", Cancer, 71: 3478-3485 (Jun. 1, 1993).

Herlyn et al., "Specific detection of anti-idiotypic immune responses in cancer patients treated with murine monoclonal antibody", J. Immunol. Method, 85: 27-38 (1985).

Ioannides et al., "T cell recognition of human tumors: implications of molecular immunotherapy of cancer", Clin. Immunol. Immunopath., 66: 91-106 (Feb. 1993).

Lanzavecchia et al., "The use of hybrid hybridomas to target human cytotoxic T lymphocytes", European Journal of Immunology, 17: 105-111 (1987).

Losman et al., "Baboon anti-idiotype antibodies mimic a carcinoembryonic antigen epitope", International Journal of Cancer, 46: 310-314 (1990).

Losman et al., "Human response against NP-4, a mouse antibody to carcinoembryonic antigen: Human anti-idiotype antibodies mimic an epitope on the tumor antigen", Proc. Natl. Aced. Sci. USA, 88: 3421-3425 (Apr. 1991).

Losman et al., "Mimicry of a carcinoembryonic antigen epitope by a rat monoclonal anti-idiotype antibody", International Journal of Cancer, 56: 580-584 (1994).

Mittelman et al., "Kinetics of the immune response and regression of metastatic lesions following development of humoral anti-high molecular weight-melanoma associated antigen immunity in three patients with advanced malignant melanoma immunized with mouse anti-idiotypic monoclonal antibody MK2-23", Cancer Research, 54, 415-421 (Jan. 15, 1994).

Pupa et al., "Activation of mononuclear cells to be used for hybrid monoclonal antibody-induced lysis of human ovarian carcinoma cells", Int. J. Cancer, 42: 455-459 (1988).

Renner et al., "Cure of xenografted human tumors by bispecific monoclonal antibodies and human T cells", Science, 264: 833-835 (May 6, 1994).

Sharkey, et al., "Enhanced clearance of radiolabeled murine monoclonal antibody by a syngeneic anti-idiotype antibody in tumor-bearing nude mice", International Journal of Cancer, 61: 266-273 (1992).

Traub et al., "Anti-idiotype antibodies in cancer patients receiving monoclonal antibody to carcinoembryonic antigen", Cancer Research, 48: 4002-4006 (Jul. 15, 1988).

VanDijk et al., "Induction of tumor-cell lysis by bi-specific monoclonal antibodies recognizing renal-cell carcinoma and CD3 antigen", Int. J. Cancer, 43: 344-349 (1989).

Irvine et al, "Compar. of CEA-recomb. Vaccinia Virus, Puri. CEA, & Anti-Idiotype Antibody Bearing Image of CEA Epitope in Tretm. & Preven. CEA-Expressing Tumors", Vaccine Research, vol. 2 No. 2, (1993) pp. 79-94.

Kos et al., "Requirement for Natural Killer Cells in the Induction of Cytotocxic T Cells Consisting of Antibody- . . . ", The Journal of Immunology, p. 578-584, (1995).

Gross et al., "Expression of Immunoglobulin T-cell Receptor Chimeric Molecules as Functional Receptors with Antibody-Type Specificity", Proced. of Natl. Acad. Sci., vol. 86, (1989), pp. 10024-10028.

Pawlak-Byczkowaka et al., "Two New Monoclonal Antibodies, EPB-1 and EPB-2, Reactive With Human Lymphoma", Cancer Research, vol. 49:4568-4577 (Aug. 1989).

Yu et al., "Peptide-Antib. Conjug. Turn. Ther. MHC-Class-II-Restri. Tet. Tox. Peptide Coup. Anti-Ig Lght. Cha. Antib. Indu. Cytoto. Lysis Hum. B-Cell Lymp. Specif. CD4 T Cells", Int. J. Cancer, vol. 56, p. 244-248, (1994).

Van Duk et al., "Bispecific Antibodies Reactive with the Multi-drug Resistance Related Glycoprotein and CD3 Induce Lysis of Multi-drug Resistance Tumor Cells", Internat. Journal of Cancer, vol. 44, (1989) pp. 738-743.

Morton et al., "Deliv. Nascent MHC Cla. II-Invar. Cha. Complx. Lysoso. Comprt. Proteo. Invar. Cha. Cysteine Protease. Prece. Peptide Bind. B-Lympho. Cells", Journal Immunology, vol. 154, p. 137-150, (1995).

Shan et al., "Constitutive Endocytosis & Degradation of CD22 by Human B Cells", The Journal of Immunology, vol. 154, p. 4466-4475, (1995).

Jessup, et al., "Adhesion to Carcinoembryonic antigen by Human Colorectal Carcinoma Cells Involves At Least Two Epitopes", Int. J. Cancer, vol. 55, p. 262-268 (1993).

Xu, et al., "The Novelty of Antigen-Processing Compartments", Cutting Edge Commentary Immunology, Journal of Immunology, p. 1652-1654 (1995).

Peters, et al., "Segregation of MHC Class II Molecules From MHC Class I Molecules Golgi Complex for Trans. to Lysosomal Compartments", Nature, vol. 349, p. 669-676, (1991).

Amigorena, et al., "Transient Accumulation of New Class II MHC Molecules in a Novel Endocytic Comprt. in B Lymphocytes", Nature, vol. 369, p. 113-120, (1994).

Waldemann, Science, 252:1657-1662, (1991).

Goldenberg, CA Cancer J. Clin., 44:43-64, (1994).

Kroesen et al., Cancer Immunol. Immunother., 37:400-407, (1993).

Wagner, et al., Biotechnology Therapeutics, 3(1&2):81-89, (1992).

Singh et al, "Protein engineering of antibodies" Crit. Rev. Biotech. vol. 12, No. 5/6 pp. 437-162, (1992).

Roitt et al., Immunol. 3rd ed, Moshy, London, p. 87 (1993).

Moldenbauek, G. Immunol. 96:473-484 (1999).

O'Boyle, K.P. et al., "Potentiation of Antiproliferative Effects of Monoclonal antibody Lym-1 and Immunoconjugate Lym-1-gelonin on Human Burkitt's Lymphoma Cells with y-lnterferon and Tumor Necrosis Factor" Journal of Immunotherapy 18(4):221-230 1996.

Amigorena et al., "Transient accumulation of new class II MHC molecules in a novel endocytic compartment in B lymphocytes" Nature 369:113-120 (1994).

Becker et al., "Expression of a Hybrid Immunoglobulin-T Cell Receptor Protein in Transgenic Mice", Cell, 58:911-921 (Sep. 1989).

Becker, S., "Inteferon-γ Accelerates Immune Proliferation via its Effect on Monocyte HLA-DR Expression", Cell. Immunol. Mar. 1985;91(1):301-7.

Bohlen et al., "Idiotype vaccination strategies against a murine B-cell lymphoma: Dendritic cells loaded with idiotype and bispecific idiotype x anti-class II antibodies can protect against tumor growth", Cytokines Mol. Ther. Dec. 1996;2(4):231-8.

Bolhuis et al., "T Cell Targeting in Cancer Therapy", Cancer Immunol. Immunother., 34:1-8 (1991).

Bolhuis et al., "Engineering T Lymphocyte Antigen Specificity", J. Cell. Biochem. 47:306-310, (1991).

Carayanniotis et al., "Delivery of synthetic peptides by anti-class II MHC monovalent antibodies induces specific adjuvant-free IgG responses in vivo", Mol. Immunol. 25(9):907-911 (1988).

Cohen et al., "Cancer Vaccines Get a Shot in the Arm", Science 262:841-843 (1993).

Durrant et al., "An idiotypic replica of carcinoembryonic antigen inducing cellular and humoral responses directed against human colorectal tumours", Int. J. Cancer 50:811-816 (1992).

Eshhar et al., "Chimeric T cell receptor which incorporates the anti-tumour specificity of a monoclonal antibody with the cytolytic activity of T cells: a model system for immunotherapeutical approach", Br. J. Cancer 62:27-29, 1990.

Eshhar et al., "Specific activation and targeting of cytotoxic lymphocytes through chimeric single chains consisting of antibody-binding domains and the γ or ζ subunits of the immunoglobulin and T-cell receptors", Proc. Natl. Acad. Sci. USA, 90:720-724 (1993).

Fagerberg et al., "Induction of an immune network cascade in cancer patients treated with monoclonal antibodies (ab1)", Cancer Immunol. Immunother. 37:264-270 (1993).

Goldenberg et al., "Monoclonal Antibodies in Cancer Detection and Therapy", Am. J. Med. 94(3):297-312 (1993).

Goldenberg et al., "New Developments in Monoclonal Antibodies for Cancer Detection and Therapy", CA Cancer J. Clin. 44(1):43-64 (1994).

Goverman et al., "Chimeric immunoglobulin-T cell receptor proteins form functional receptors: implications for T cell receptor complex formation and activation", Cell 60:929-939 (1993).

Gross et al., "Generation of effector T cells expressing chimeric T cell receptor with antibody type-specificity", Transp. Proc. 21(1):127-130 (Feb. 1989).

Gross et al., "Expression of immunoglobulin-T-cell receptor chimeric molecules as functional receptors with antibody-type specificity", Proc. Natl. Acad. Sci. USA 86:10024-10028 (Dec. 1989).

Hansen et al., "Characterization of second-generation monoclonal antibodies against carcinoembryonic antigen" Cancer 71(11):3478-3485 (1993).

Herlyn et al., "Specific detection of anti-idiotypic immune responses in cancer patients treated with murine monoclonal antibody", J. Immunol. Methods 85:27-38 (1985).

Herlyn et al., "Anti-idiotype immunization of cancer patients: Modulation of the immune response", Proc. Natl. Acad. Sci. USA 84:8055-8059 (1987).

Ioannides et al., "T cell recognition of human tumors: implications for molecular immunotherapy of cancer", Clin. Immunol. Immunopath. 66:91-106 (Feb. 1993).

Irvine et al., "Comparison of CEA-Recombinant Vaccinia Virus, Purified CEA, and an Anti-Idiotype Antibody Bearing the Image of a CEA Epitope in the Treatment and Prevention of CEA-Expressing Tumors", Vaccine Res. 2(2):79-94 (1993).

Jessup et al., "Adhesion of carcinoembryonic antigen by human colorectal carcinoma cells involves at least two epitopes", Int. J. Cancer 55:262-268 (1993).

Kos et al., "Requirement for Natural Killer Cells in the Induction of Cytotoxic T Cells", J. Immunol. 155:578-584 (1995).

Kroesen et al., "Local antitumour treatment in carcinoma patients with bispecific-monoclonal-antibody-redirected T cells", Cancer Immunol. Immunother. 37(6):400-407 (1993).

Lanzavecchia et al., "The use of hybrid hybridomas to target human cytotoxic T lymphocytes", Eur. J. Immun. 17:105-111 (1987).

Losman et al., "Baboon anti-idiotype antibodies mimic a carcinoembryonic antigen epitope", Int. J. Cancer 46:310-314 (1990).

Losman et al., "Human response against NP-4, a mouse antibody to carcinoembryonic antigen: Human anti-idiotype antibodies mimic an epitope on the tumor antigen", Proc. Natl. Acad. Sci. USA 88:3421-3425 (Apr. 1991).

Mittelman et al., "Kinetics of the immune response and regression of metastatic lesions following development of humoral anti-high molecular weight-melanoma associated antigen immunity in three patients with advanced malignant melanoma immunized with mouse antiidiotypic monoclonal antibody MK2-23", Cancer Res. 54:415-421(1994).

Morton et al., Delivery of Nascent MHC Class II-Invariant Chain Complexes to Lysosomal Compartments and Proteolysis of Invariant Chain by Cysteine Proteases Preceded Peptide Binding in B-Lymphoblastoid Cells, J. Immunol. 154:137-150 (1995).

Nepom et al., "Induction of immunity to a human tumor marker by in vivo administration of anti-idiotypic antibodies in mice", Proc. Natl. Acad. Sci. USA 81:2864-2867 (1984).

Peters et al., "Segregation of MHC Class II molecules from MHC Class I molecules in the Golgi complex for trasport to lysosomal compartments", Nature 349:669-676 (1991).

Powell et al., "Induction of effective immunity to moloney murine sarcoma virus using monoclonal anti-idiotypic antibody as immunogen", J. Immunol. 142(4):1318-1324 (1989).

Pupa et al., "Activation of mononuclear cells to be used for hybrid monoclonal antibody-induced lysis of human ovarian carcinoma cells", Int. J. Cancer 42:455-459 (1988).

Renner et al., "Cure of xenografted human tumors by bispecific monoclonal antibodies and human T cells", Science 264:833-835 (1994).

Roitt et al., Immunology, 3rd Ed., Mosby, London, 1993, p. 6.9.

Rosenthal et al., "Human tumor vaccines and genetic engineering of tumors with cytokine and histocompatibility genes to enhance immunogenicity", Curr. Opin. Oncol. 6:611-615 (1994).

Sandhu, J., "Protein Engineering of Antibodies", Crit. Rev. Biotech. 12(5/6):437-462 (1992).

Shan et al., "Constitutive Endocytosis and Degradation of CD22 by Human B Cells", J. Immunol. 154:4466-4475 (1995).

Sharkey et al., "Enhanced clearance of radiolabeled murine monoclonal antibody by a syngeneic anti-idiotype antibody in tumor-bearing nude mice", Int. J. Cancer 51(2):266-273 (1992).

Stein et al., "Neonatal administration of idiotype or antiidiotype primes for protection against *Escherichia coli* K13 infection in mice", J. Exp. Med. 160(4):1001-11 (1984).

Traub et al., "Antiidiotype Antibodies in Cancer Patients Receiving Monoclonal Antibody to Carcinoembryonic Antigen", Cancer Res. 48:4002-4006 (1988).

Tsang et al., "A Recombinant CEA-Vaccinia Vaccine Induces a CEA-Specific Cytotoxic T-cell Response in Carcinoma Patients", Proc. Amer. Assoc. Cancer Res. vol. 36, p. 249, Abstract #1483 (1995).

Van Dijk et al., "Induction of tumor-cell lysis by bi-specific monoclonal antibodies recognizing renal-cell carcinoma and CD3 antigen", Int. J. Cancer 43:344-349 (1989).

Van Duk et al., "Bispecific antibodies reactive with the multidrug-resistance-related glycoprotein and CD3 induce lysis of multidrug-resistant tumor cells", Int. J. Cancer 44:738-743 (1989).

Van Kaer, L., "Accessory Proteins that Control the Assembly of MHC Molecules with Peptides", Immunologic Res. 23-2/3:205-214 (2001).

Wagner et al., "Immunotherapy of advanced ovarian carcinomas by activation of the idiotypic network", Biotechnol. Ther. 3(1-2):81-89 (1992).

Waldmann et al., "Monoclonal Antibodies in Diagnosis and Therapy", Science 252:1657-1662 (1991).

Xu et al., "The Novelty of Antigen-Processing Compartments", J. Immunol. 155(4):1652-4 (1995).

Yu et al., "Peptide-antibody conjugates for tumour therapy: a MHC-class-II-restricted tetanus toxin peptide coupled to an anti-Ig light chain antibody can induce cytotoxic lysis of a human B-cell lymphoma by specific CD4 T cells", Int. J. Cancer 56:244-248 (1994).

* cited by examiner

USE OF IMMUNOCONJUGATES TO ENHANCE THE EFFICACY OF MULTI-STAGE CASCADE BOOSTING VACCINES

CROSS-REFERENCE TO RELATED APPLICATIONS

This application is a continuation-in-part of U.S. Ser. No. 08/268,129, filed on Jul. 6, 1994, which is incorporated by reference in its entirety.

BACKGROUND OF THE INVENTION

1. Field of the Invention

The present invention relates to methods for inducing humoral and cellular immune responses against malignant cells and infectious agents. In particular, this invention is directed to methods for producing an integrated immunologic response against tumor cells or infectious agents using immunoconjugates comprising antibodies and anti-idiotype antibodies that mimic an epitope of an antigen that is associated with a tumor or infectious agent. The present invention also is directed to a method for augmenting such an integrated response using immunoconjugates, antibodies, anti-idiotype antibodies and cytokines.

2. Background

One of the major goals of immunotherapy is to harness a patient's immune system against tumor cells or infectious organisms. With regard to cancer therapy, the objective is to direct the patient's immune system against tumor cells by targeting antigens that are associated with tumor cells, but not normal counterparts. Although these tumor associated antigens (TAA) have been difficult to identify, certain tumor cells express antigens that are normally not expressed, or expressed at very low levels, in adult life but present during fetal development. One example of such oncofetal TAA is α-fetoprotein, which is expressed by liver cancer cells. Another oncofetal TAA is the carcinoembryonic antigen (CEA), which is expressed in most adenocarcinomas of entodermally-derived digestive system epithelia, as well as in breast tumor cells and non-small-cell lung cancer cells. Thomas et al., *Biochim. Biophys. Acta* 1032: 177 (1990).

The administration of anti-idiotype antibodies (Ab2) mimicking TAA represents one of the most promising approaches to cancer immunotherapy. Goldenberg, *Amer. J. Med.* 94: 297 (1993). Ab2 are antibodies directed against the variable regions of conventional antibodies (Ab1). Since Ab2 and antigen can bind with the same regions of the Ab1-combining site, certain Ab2 (termed "Ab2β" or "internal-image" antibodies) can mimic the three dimensional structure of the nominal antigen. Jerne et al., *EMBO J.* 1: 243 (1982); Losman et al., *Int. J. Cancer* 46: 310 (1990); Losman et al., *Proc. Nat'l Acad. Sci. USA* 88: 3421 (1991); Losman et al., *Int. J. Cancer* 56: 580 (1994). Individuals immunized with Ab2β can develop anti-anti-antibodies (Ab3), some of which (Ab1') can bind the nominal antigen.

The antigen mimicry properties of anti-idiotype antibodies have led to the use of Ab2β as surrogate antigens (or idiotype vaccines), when the nominal antigen is not readily available or when the host is tolerant to the nominal antigen. In experimental systems, immunization with Ab2β mimicking certain TAA creates specific immunity to the TAA and protect against subsequent tumor growth. See, for example, Nepom et al., *Proc. Nat'l Acad. Sci. USA* 81: 2864 (1984); Raychaudhuri et al., *J. Immunol.* 139: 271 (1987). Similarly, anti-idiotype vaccines have been developed against infectious organisms, such as *Streptococcus pneumoniae* [McNamara et al., *Science* 226: 1325 (1984)], hepatitis B virus [Kennedy et al., *Science* 223: 930 (1984)], *Escherichia coli* K13 [Stein et al., *J. Exp. Med.* 160: 1001 (1984)], *Schistosomiasis mansoni* [Kresina et al., *J. Clin. Invest.* 83: 912 (1989)], and Moloney murine sarcoma virus [Powell et al., *J. Immunol.* 142: 1318 (1989)].

Cancer patients receiving an anti-TAA of animal origin will usually produce antibodies to the Ab1 and these anti-immunoglobulin antibodies include Ab2. Herlyn et al., *J. Immunol. Methods* 85: 27 (1985); Traub et al., *Cancer Res.* 48: 4002 (1988). The anti-idiotype response also may include the generation of T cells (T2). Fagerberg et al., *Cancer Immunol. Immunother.* 37: 264 (1993). Moreover, Ab2 may subsequently induce a humoral and cellular anti-anti-idiotypic response, Ab3 and T3, respectively, which may recognize the same epitope as Ab1. Id.

Thus, an opportunity exists to provide an approach to immunotherapy utilizing both humoral and cellular immune systems. The applicant has developed methods to provoke an integrated response against tumor cells, as well as against infectious agents. Furthermore, the applicant has developed methods to amplify the immune cascade.

SUMMARY OF THE INVENTION

Accordingly, it is an object of the present invention to provide a method for inducing humoral and cellular immune responses against tumor cells and infectious agents using vaccines comprising an antibody that binds with the HLA-DR-complex and an antigenic peptide that comprises at least one epitope of a TAA or an antigen associated with an infectious agent. It is a further object of this invention to provide a method to amplify such an integrated response using antibodies and cytokines.

Another object of this invention is to provide methods for inducing humoral and cellular immune responses in a mammal against a tumor that expresses a tumor associated antigen comprising the administration of a vaccine comprising an antibody component that binds with the HLA-DR-complex and an antigenic peptide that induces a major histocompatibility (MHC)-restricted immune response.

These and other objects are achieved, in accordance with one embodiment of the present invention by the provision of a method for inducing humoral and cellular immune responses in a mammal against a tumor that expresses a tumor associated antigen (TAA) or against a disease caused by an infectious agent, comprising the steps of:

(a) administering a first vaccine intradermally to the mammal, wherein the first vaccine comprises an immunoconjugate that comprises:
   (i) an antibody component that binds with the HLA-DR-complex, and
   (ii) an antigenic peptide, wherein the antigenic peptide comprises at least one epitope of a TAA or an antigen associated with the infectious agent,
and
(b) administering the vaccine intravenously to the mammal.

The antibody component of step (a) may be selected from the group consisting of (a) a murine monoclonal antibody; (b) a humanized antibody derived from a murine monoclonal antibody; (c) a human monoclonal antibody; and (d) an antibody fragment derived from (a), (b) or (c), wherein the antibody fragment is selected from the group consisting of F(ab')$_2$, F(ab)$_2$, Fab', Fab, Fv, sFv and minimal recognition unit.

The present invention also is directed to a method further comprising the step of (c) administering interferon-γ, interleukin-2, or interleukin-12 prior to and during step (b). Alternatively, interleukin-2, interferon-γ and interleukin-12 may be administered prior to and during step (b).

The present invention is further directed to a method for inducing humoral and cellular immune responses in a mammal against a tumor that expresses a tumor associated antigen (TAA), comprising the steps of:
(a) administering a first vaccine intradermally to the mammal, wherein the first vaccine comprises an immunoconjugate that comprises:
  (i) an antibody component that binds with the HLA-DR-complex, and
  (ii) an antigenic peptide that induces a major histocompatibility (MHC)-restricted immune response, and
(b) administering the vaccine intravenously to the mammal.

The antibody component of step (a) is selected from the group consisting of (a) a murine monoclonal antibody; (b) a humanized antibody derived from a murine monoclonal antibody; (c) a human monoclonal antibody; and (d) an antibody fragment derived from (a), (b) or (c), in which the antibody fragment is selected from the group consisting of F(ab')$_2$, F(ab)$_2$, Fab', Fab, Fv, sFv and minimal recognition unit. A suitable antigenic peptide, for example, is tetanus toxin P2 peptide.

The present invention also is directed to a method further comprising the step of (c) administering interferon-γ, interleukin-2, or interleukin-12 prior to and during step (b). Alternatively, interleukin-2, interferon-γ and interleukin-12 may be administered prior to and during step (b).

The present invention is further directed to a method comprising the alternative step (c) of administering a second vaccine intravenously to the mammal, wherein the second vaccine comprises an immunoconjugate that comprises:
  (i) an antibody component that binds with a TAA, and
  (ii) an antigenic peptide that induces a MHC-restricted immune response.

An example of a suitable antigenic peptide of the second vaccine is tetanus toxin P2 peptide. The present invention also is direct to a method further comprising the step (d) of administering at least one cytokine selected from the group consisting of interleukin-2, interleukin-12 and interferon-γ prior to and during step (c).

The present invention also is directed to a method for inducing humoral and cellular immune responses in a mammal against a tumor that expresses carcinoembryonic antigen (CEA), comprising the steps of:
(a) administering a first vaccine to the mammal, wherein the first vaccine comprises an antibody component that binds with CEA, and wherein the antibody component is conjugated with a soluble immunogenic carrier protein; and
(b) administering a second vaccine to the mammal, wherein the second vaccine comprises an anti-idiotype antibody component that mimics an epitope of the CEA, and wherein the anti-idiotype antibody component is conjugated with a soluble immunogenic carrier protein, and
(c) administering a third vaccine to the mammal, wherein the third vaccine comprises an immunoconjugate comprising an antigenic peptide that comprises an epitope of CEA, and an antibody component that binds with the HLA-DR complex.

A suitable antigenic peptide of the third vaccine comprises the A3B3 domain of CEA. Moreover, the antigenic peptide of the third vaccine can comprise a minimal recognition unit of an anti-idiotype antibody that mimics an epitope of CEA. In these methods, the antibody component of step (a) is selected from the group consisting of:
(a) a murine monoclonal Class III anti-CEA antibody;
(b) a humanized antibody derived from a murine monoclonal Class III anti-CEA antibody;
(c) a human monoclonal anti-CEA antibody; and
(d) an antibody fragment derived from (a), (b) or (c), wherein the antibody fragment is selected from the group consisting of F(ab')$_2$, F(ab)$_2$, Fab', Fab, Fv, sFv and minimal recognition unit.

Furthermore, the anti-idiotype antibody component is selected from the group consisting of:
(a) a polyclonal antibody that binds with the variable region of a Class III anti-CEA antibody;
(b) a murine monoclonal antibody that binds with the variable region of a Class III anti-CEA antibody;
(c) a humanized antibody derived from (b);
(d) a human monoclonal antibody that binds with the variable region of a Class III anti-CEA antibody;
(e) a subhuman primate antibody that binds with the variable region of a Class III anti-CEA antibody; and
(f) an antibody fragment derived from (a), (b), (c), (d) or (e), in which the antibody fragment is selected from the group consisting of F(ab')$_2$, F(ab)$_2$, Fab', Fab, Fv, sFv and minimal recognition unit.

The present invention also is directed to methods further comprising the step of (c) administering interferon-γ, interleukin-2, or interleukin-12 prior to and during the administration of the second vaccine. As an alternative, interleukin-2, interleukin-12 and interferon-γ can be administered prior to and during the administration of the second vaccine.

DETAILED DESCRIPTION

1. Definitions

In the description that follows, a number of terms are used extensively. The following definitions are provided to facilitate understanding of the invention.

A structural gene is a DNA sequence that is transcribed into messenger RNA (mRNA) which is then translated into a sequence of amino acids characteristic of a specific polypeptide.

A promoter is a DNA sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter.

An isolated DNA molecule is a fragment of DNA that is not integrated in the genomic DNA of an organism. For example, a cloned T cell receptor gene is a DNA fragment that has been separated from the genomic DNA of a mammalian cell. Another example of an isolated DNA molecule is a chemically-synthesized DNA molecule that is not integrated in the genomic DNA of an organism.

An enhancer is a DNA regulatory element that can increase the efficiency of transcription, regardless of the distance or orientation of the enhancer relative to the start site of transcription.

Complementary DNA (cDNA) is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term expression refers to the biosynthesis of a gene product. For example, in the case of a structural gene, expression involves transcription of the structural gene into mRNA and the translation of mRNA into one or more polypeptides.

A cloning vector is a DNA molecule, such as a plasmid, cosmid, or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An expression vector is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

A tumor associated antigen is a protein normally not expressed, or expressed at very low levels, by a normal counterpart. Examples of tumor associated antigens include α-fetoprotein and carcinoembryonic antigen (CEA).

As used herein, an infectious agent denotes both microbes and parasites. A "microbe" includes viruses, bacteria, *rickettsia*, mycoplasma, protozoa, fungi and like microorganisms. A "parasite" denotes infectious, generally microscopic or very small multicellular invertebrates, or ova or juvenile forms thereof, which are susceptible to antibody-induced clearance or lytic or phagocytic destruction, such as malarial parasites, spirochetes, and the like.

In the present context, an anti-CEA MAb is a Class III MAb, as described by Primus et al., *Cancer Research* 43: 686 (1983) and by Primus et al., U.S. Pat. No. 4,818,709, which are incorporated by reference.

As used herein, an Ab1 is an antibody that binds with a tumor associated antigen or an antigen associated with an infectious agent.

An anti-idiotype antibody (Ab2), as used herein, is an antibody that binds with an Ab1. Importantly, an Ab2 binds with the variable region of Ab1 and thus, an Ab2 mimics an epitope of a tumor associated antigen or an epitope of an infectious agent associated antigen.

An antibody fragment is a portion of an antibody such as F(ab')$_2$, F(ab)$_2$, Fab', Fab, and the like. Regardless of structure, an antibody fragment binds with the same antigen that is recognized by the intact antibody. For example, an anti-CEA Mab (Ab1) fragment binds with CEA, while an Ab2 fragment binds with the variable region of the Ab1 and mimics an epitope of CEA.

The term "antibody fragment" also includes any synthetic or genetically engineered protein that acts like an antibody by binding to a specific antigen to form a complex. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker ("sFv proteins"), and minimal recognition units consisting of the amino acid residues that mimic the hypervariable region.

Humanized antibodies are recombinant proteins in which murine complementarity determining regions of MAb have been transferred from heavy and light variable chains of the murine immunoglobulin into a human variable domain.

As used herein, the term antibody component includes both an entire antibody and an antibody fragment.

2. Production of Monoclonal Antibodies, Humanized Antibodies, Primate Antibodies and Human Antibodies Rodent monoclonal antibodies to specific antigens may be obtained by methods known to those skilled in the art. See, for example, Kohler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

A wide variety of monoclonal antibodies against tumor associated antigens or infectious agents have been developed. See, for example, Goldenberg et al., international application publication No. WO 91/11465 (1991), and Goldenberg, international application publication No. WO 94/04702 (1994), each of which is incorporated by reference in its entirety.

An example of a suitable Mab is a Class III anti-CEA Mab. Conventional antisera raised against CEA usually contain antibodies that react with a group of substances closely related to CEA. The major members of this family of CEA-related antigens are (1) the normal cross-reactive antigen (NCA), which shares a similar tissue distribution with CEA, and (2) meconium antigen (MA), which shares almost identical physiochemical properties with CEA. The first panel of monoclonal antibodies (MAb) that defined NCA-cross-reactive, MA-cross-reactive, and CEA-specific epitopes on the CEA molecule were described by Primus et al., *Cancer Research* 43: 686 (1983). In particular, three classes of anti-CEA antibody were identified: 1) Class I antibodies, which react with CEA, NCA and MA; 2) Class II antibodies, which react with CEA and MA, but not with NCA; and 3) Class III antibodies, which are specific for CEA and do not bind with NCA or MA. Methods for obtaining Class III anti-CEA MAbs are disclosed by *Primus et al., Cancer Research* 43: 686 (1983), and Primus et al., U.S. Pat. No. 4,818,709. Moreover, the production of second generation Class III anti-CEA MAbs is disclosed by Hansen et al., *Cancer* 71: 3478 (1993), which is incorporated by reference.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

In another embodiment, an antibody of the present invention is a subhuman primate antibody. General techniques for raising therapeutically useful antibodies in baboons may be found, for example, in Goldenberg et al., international patent publication No. WO 91/11465 (1991), and in Losman et al., *Int. J. Cancer* 46: 310 (1990), which is incorporated by reference.

In yet another embodiment, an antibody of the present invention is a "humanized" monoclonal antibody. That is, mouse complementarity determining regions are transferred from heavy and light variable chains of the mouse immunoglobulin into a human variable domain, followed by the replacement of some human residues in the framework regions of their murine counterparts. Humanized monoclonal antibodies in accordance with this invention are suitable for use in therapeutic methods. General techniques for cloning murine immunoglobulin variable domains are described, for example, by the publication of Orlandi et al., *Proc. Nat'l Acad. Sci. USA* 86: 3833 (1989), which is incorporated by reference in its entirety. Techniques for producing humanized MAbs are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993), each of which is hereby incorporated by reference.

In another embodiment, an antibody of the present invention is a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7: 13 (1994), Lonberg et al., *Nature* 368: 856 (1994), and Taylor et al., *Int. Immun.* 6: 579 (1994), which are incorporated by reference.

3. Production of Antibody Fragments

The present invention contemplates the use of fragments of Ab1 or Ab2. Antibody fragments can be prepared by proteolytic hydrolysis of the antibody or by expression in *E. coli* of the DNA coding for the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment directly. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of V$_H$ and V$_L$ chains. This association can be noncovalent, as described in Inbar et al., *Proc. Nat'l Acad. Sci. USA* 69: 2659 (1972). Alternatively, the variable chains can be linked by an intermolecular disulfide bond or cross-linked by chemicals such as glutaraldehyde. See, for example, Sandhu, supra.

Preferably, the Fv fragments comprise V$_H$ and V$_L$ chains which are connected by a peptide linker. These single-chain antigen binding proteins (sFv) are prepared by constructing a structural gene comprising DNA sequences encoding the V$_H$ and V$_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing sFvs are described, for example, by Whitlow et al., *Methods: A Companion to Methods in Enzymology* 2: 97 (1991). Also see Bird et al., *Science* 242:423-426 (1988), Ladner et al., U.S. Pat. No. 4,946,778, Pack et al., *Bio/Technology* 11:1271-1277 (1993), and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

4. Production of Anti-Idiotype Antibodies (Ab2)

Polyclonal Ab2 can be prepared by immunizing animals with Ab1 or fragments, using standard techniques. See, for example, Green et al., "Production of Polyclonal Antisera," in METHODS IN MOLECULAR BIOLOGY: IMMUNOCHEMICAL PROTOCOLS, Manson (ed.), pages 1-12 (Humana Press 1992). Also, see Coligan at pages 2.4.1-2.4.7.

Alternatively, monoclonal Ab2 can be prepared using Ab1 or fragments as immunogens with the techniques, described above. The preparation of a rat monoclonal Ab2 is illustrated in Example 3.

As another alternative, humanized Ab2 or subhuman primate Ab2 can be prepared using the above-described techniques.

5. Production of Bispecific Antibodies

Bispecific antibodies can be used to recruit and target T cells to a tumor cell. A bispecific antibody is a hybrid molecule that consists of nonidentical light and heavy chain pairs, providing two distinct antibody specificities. For example, bispecific antibodies have been produced with one binding site recognizing the CD3 signal transducing protein on T cells and a second binding site for a tumor-associated antigen. See, for example, Canevari et al., *Int. J. Cancer* 42: 18 (1988); Lanzaveccia et al., *Eur. J. Immunol.* 17: 105 (1987); Van Dijk et al., *Int. J. Cancer* 43: 344 (1989); and Renner et al., *Science* 264: 833 (1994).

Bispecific antibodies can be made by a variety of conventional methods, e.g., disulfide cleavage and reformation of mixtures of whole antibody or, preferably F(ab')₂ fragments, fusions of more than one hybridoma to form polyomas that produce antibodies having more than one specificity, and by genetic engineering. Bispecific antibodies have been prepared by oxidative cleavage of Fab' fragments resulting from reductive cleavage of different antibodies. See, for example, Winter et al., *Nature* 349: 293 (1991). This is advantageously carried out by mixing two different F(ab')₂ fragments produced by pepsin digestion of two different antibodies, reductive cleavage to form a mixture of Fab' fragments, followed by oxidative reformation of the disulfide linkages to produce a mixture of F(ab')₂ fragments including bispecific antibodies containing a Fab' portion specific to each of the original epitopes. General techniques for the preparation of such antibody composites may be found, for example, in Nisonhoff et al., *Arch Biochem. Biophys.* 93: 470 (1961), Hammerling et al., *J. Exp. Med.* 128: 1461 (1968), and U.S. Pat. No. 4,331,647.

More selective linkage can be achieved by using a heterobifunctional linker such as maleimide-hydroxysuccinimide ester. Reaction of the ester with an antibody or fragment will derivatize amine groups on the antibody or fragment, and the derivative can then be reacted with, e.g., an antibody Fab fragment having free sulfhydryl groups (or, a larger fragment or intact antibody with sulfhydryl groups appended thereto by, e.g., Traut's Reagent). Such a linker is less likely to crosslink groups in the same antibody and improves the selectivity of the linkage.

It is advantageous to link the antibodies or fragments at sites remote from the antigen binding sites. This can be accomplished by, e.g., linkage to cleaved interchain sulfydryl groups, as noted above. Another method involves reacting an antibody having an oxidized carbohydrate portion with another antibody which has at lease one free amine function. This results in an initial Schiff base (imine) linkage, which is preferably stabilized by reduction to a secondary amine, e.g., by borohydride reduction, to form the final composite. Such site-specific linkages are disclosed, for small molecules, in U.S. Pat. No. 4,671,958, and for larger addends in U.S. Pat. No. 4,699,784.

In the present context, a bispecific antibody comprises binding moieties for T cells and an antigen that is associated with a tumor cell or infectious agent. For example, a CEA binding moiety can be derived from a Class III Mab and the T cell-binding moiety can be derived from anti-CD3 Mab. Methods for preparing anti-CD3 antibodies are well-known to those of skill in the art. See, for example, Canevari et al., supra, Van Dijk et al., supra, Hansen et al., "Human T Lymphocyte Cell Surface Molecules Defined by the Workshop Monoclonal Antibodies (T Cell Protocol)," in LEUKOCYTE TYPING: HUMAN LEUKOCYTE MARKERS DETECTED BY MONOCLONAL ANTIBODIES, Bernard et al., (eds.) pages 195-212 (Springer-Verlag 1984); and U.S. Pat. No. 4,361,549. Alternatively, anti-CD3 antibodies can be obtained from commercial sources such as Boehringer Mannheim Corp. (Indianapolis, Ind.; Cat. No. 1273 485) and the American Type Culture Collection (Rockville, Md.; ATCC CRL 8001 [OKT-3]).

For example, a bispecific antibody can be prepared by obtaining an F(ab')₂ fragment from an anti-CEA Class III Mab, as described above. The interchain disulfide bridges of the anti-CEA Class III F(ab')₂ fragment are gently reduced with cysteine, taking care to avoid light-heavy chain linkage, to form Fab'-SH fragments. The SH group(s) is (are) activated with an excess of bis-maleimide linker (1,1'-(methylenedi-4, 1-phenylene)bis-malemide). The anti-CD3 Mab is converted to Fab'-SH and then reacted with the activated anti-CEA Class III Fab'-SH fragment to obtain a bispecific antibody.

Alternatively, such bispecific antibodies can be produced by fusing two hybridoma cell lines that produce anti-CD3 Mab and anti-CEA Class III Mab. Techniques for producing tetradomas are described, for example, by Milstein et al., *Nature* 305: 537 (1983) and Pohl et al., *Int. J. Cancer* 54: 418 (1993).

Finally, bispecific antibodies can be produced by genetic engineering. For example, plasmids containing DNA coding for variable domains of an anti-CEA Class III Mab can be introduced into hybridomas that secrete anti-CD3 antibodies. The resulting "transfectomas" produce bispecific antibodies that bind CEA and CD3. Alternatively, chimeric genes can be designed that encode both anti-CD3 and anti-CEA binding domains. General techniques for producing bispecific antibodies by genetic engineering are described, for example, by Songsivilai et al., *Biochem. Biophys. Res. Commun.* 164: 271 (1989); Traunecker et al., *EMBO J.* 10: 3655 (1991); and Weiner et al., *J. Immunol.* 147: 4035 (1991).

6. Preparation of Immunoconjugates

The present invention contemplates the use of immunoconjugates to augment the immune response. In the present context, an "immunoconjugate" is a molecule comprising an antibody component and an antigenic peptide. An immunoconjugate retains the immunoreactivity of the antibody component, i.e., the antibody moiety has about the same, or slightly reduced, ability to bind the cognate antigen after conjugation as before conjugation.

Suitable antigenic peptides comprise either at least one epitope of a tumor associated antigen or at least one epitope of an antigen associated with an infectious agent. A general overview of useful tumor associated antigens and of infectious agent antigens is provided above.

The A3B3 epitope of CEA is an example of a preferred tumor-associated, antigenic peptide. Jessup et al., *Int. J. Cancer* 55: 262 (1993); Zhou et al., *Cancer Res.* 53: 3817 (1993); and Hefta et al., *Cancer Res.* 52: 5647 (1992). Peptides containing CEA epitopes can be produced by recombinant DNA methodology. Id. Alternatively, synthetic peptides can be produced using the general techniques described below.

Useful antigenic peptides also include epitopes of antigens from infectious agents, such as *E. coli* endotoxin core polysaccharide. See, for example, Greenman et al., *J. Am. Med. Assoc.* 266: 1097 (1991).

In the present context, particularly useful immunoconjugates deliver antigenic peptides to cells for antigen presentation. See, for example, Wyss-Coray et al., *Cell. Immunol.* 139: 268 (1992), which describes the use of an antibody-peptide construct to deliver antigenic peptides to T cells. Examples of such antigenic peptides include the tetanus toxoid peptide P2 with an N-terminal cysteine, CQYIKANSKFIGITEL (C+tt830-844; C-ttp2; SEQ ID NO:1), and tetanus toxoid peptide P30 with a C-terminal cysteine, FNNFTVSFWL-RVPKVSASHLEC (tt947-967+C; SEQ ID NO:2).

Additional antigenic peptides can be derived from single complementarity-determining regions (CDRs) of an anti-idiotype antibody. Such CDR peptides, or "minimal recognition units," can be obtained, for example, using the polymerase chain reaction to synthesize the variable region from RNA of antibody-producing cells. See, for example, Larrick et al., *Methods: A Companion to Methods in Enzymology* 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995). Minimal recognition units also can be obtained by synthesizing peptides having amino acid sequences of known antibodies. See, for example, Kabat et al., SEQUENCES OF PROTEINS OF IMMUNOLOGICAL INTEREST, U.S. Department of Health and Human Services (1983). General methods for peptide synthesis can be found, for example, in Bodanszky et al., THE PRACTICE OF PEPTIDE SYNTHESIS (Springer-Verlag 1984); Bodanszky, PRINCIPLES OF PEPTIDE SYNTHESIS (Springer-Verlag 1984); Hancock et al., "Synthesis of Peptides for Use as Immunogens," in METHODS 1N MOLECULAR BIOLOGY, VOL. 10: IMMUNOCHEMICAL PROTOCOLS, Manson (ed.) pages 23-32 (The Humana Press, Inc. 1992).

Antigenic peptides can be attached at the hinge region of a reduced antibody component via disulfide bond formation. For example, the tetanus toxoid peptides described above were constructed with a single cysteine residue that is used to attach the peptide to an antibody component. As an alternative, such peptides can be attached to the antibody component using a heterobifunctional cross-linker, such as N-succinyl 3-(2-pyridyldithio)proprionate (SPDP). Yu et al., *Int. J. Cancer* 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995).

As discussed above, an antigenic peptide can be attached to a reduced thiol group in the hinge region of an antibody component. Alternatively, the antigenic peptide can be conjugated via a carbohydrate moiety in the Fc region of the antibody. The carbohydrate group can be used to increase the loading of the same peptide that is bound to a thiol group, or the carbohydrate moiety can be used to bind a different peptide.

Methods for conjugating peptides to antibody components via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313. The general method involves reacting an antibody component having an oxidized carbohydrate portion with a carrier polymer that has at least one free amine function and that is loaded with a plurality of peptide. This reaction results in an initial Schiff base (imine) linkage, which can be stabilized by reduction to a secondary amine to form the final conjugate.

The Fc region is absent if an antibody fragment is used as the antibody component of the immunoconjugate. However, it is possible to introduce a carbohydrate moiety into the light chain variable region of an antibody or antibody fragment. See, for example, Leung et al., *J. Immunol.* 154: 5919 (1995); Hansen et al., U.S. Pat. No. 5,443,953 (1995). The engineered carbohydrate moiety is used to attach the antigenic peptide.

7. The Use of Immunoconjugates, Antibodies and Cytokines to Amplify the Humoral and Cellular Immune Response Against Tumor Cells and Infectious Agents The present invention contemplates the therapeutic use of immunoconjugates, Ab1, Ab2 generated against Ab1, and fragments of either Ab1 or Ab2. These immunoconjugates, antibodies and antibody fragments can be used as vaccines to induce both humoral and cellular immune responses in the recipient mammal. Moreover, the administration of immunoconjugates, Ab1 and/or bispecific antibodies can be used to amplify the integrated immune response.

According to one method of the present invention, a mammal is immunized with a vaccine comprising Ab1 or fragments thereof, to induce the production of Ab2 and T cells (T2 cells). After the mammal begins to produce T2 cells, the mammal may be given Ab1, or fragments thereof, by intravenous administration to expand the T2 cell mass. An additional advantage of this second administration is that the antibodies or fragments bind with cognate antigen on cancer cells or infectious organisms and thus, serve as targets for T2 cells. Methods for detecting the production of T cells that react with specific antibodies are well-known to those of ordinary skill in the art. See, for example, Fagerberg et al., *Cancer Immunol. Immunother.* 37: 264 (1993), which is incorporated by reference.

According to a preferred method, a mammal is subsequently immunized with a vaccine comprising Ab2, or fragments thereof, to induce the formation of Ab3 and T cells that recognize Ab2 (T3 cells). An advantage of this subsequent Ab2 vaccination is that cells expressing a tumor associated antigen or infectious agent antigen are destroyed by T3 cells directed to the antigen, and by T2 cells directed to Ab3, which also is bound by the antigen. Example 4 illustrates a method of treatment comprising the administration of an Ab1 vaccine, Ab1 (or fragments), and an Ab2 vaccine.

In addition, the T2 response may be further amplified by the intravenous administration of Ab1 antibodies or fragments after Ab2 vaccination.

It is possible that the efficacy of an Ab2 vaccine may be decreased by the presence of circulating Ab1 antibody components, which have been administered intravenously. Therefore, it is advantageous to clear circulating Ab1 components prior to the administration of an Ab2 vaccine. One method that can be used to achieve Ab1 clearance is to use Ab1 antibodies that have been conjugated with biotin. In this way, circulating biotinylated Ab1 can be cleared prior to Ab2 vaccination by the intravenous administration of avidin. Preferably, clearance with avidin is performed one to two days after the intravenous administration of Ab1 (or fragments thereof). This antibody clearance technique is described by Goldenberg, international application publication No. WO 94/04702 (1994).

In an alternative method of immunotherapy, a mammal is immunized with an Ab1 vaccine, treated with Ab1 (or fragments) to saturate a high percentage of tumor or infectious agent antigen sites and then, hyperimmunized with Ab1 vaccine to generate large numbers of cytotoxic lymphocytes directed against cells coated with Ab1 (or fragments thereof).

The immunoconjugates of the present invention are used to further enhance the efficacy of antibody vaccine administration. According to one method, an antibody or antibody fragment is conjugated with a peptide capable of inducing a strong major histocompatibility complex (MHC)-restricted immune response. An example of a suitable antigenic peptide is the tetanus toxin P2 peptide, described above. Such a peptide can be conjugated, for example, to the IMMU-LL1 (EPB-1) antibody, which binds with the HLA-DR-complex on the plasma membrane of macrophages, monocytes, and B-lymphocytes. Palak-Byczkowska et al., *Cancer Res.* 49: 4568 (1989). An IMMU-LL1 vaccine first is injected intradermally to establish primary sensitization and then, the vaccine is administered intravenously to boost the immune response.

Once a mammal has been sensitized by treatment with an immunoconjugate, such as an IMMU-LL1-P2 vaccine, the mammal can be treated with an immunoconjugate that directs the immune response to tumor cells. For example, an immunoconjugate comprising humanized LL2 and P2 can be used to target CD22-bearing tumor cells. LL2 is described by Goldenberg et al., *J. Clin. Oncol.* 9: 548 (1991), and by Murthy et al., *Eur. J. Nucl. Med.* 19: 394 (1992). In this way, the sensitizing peptide (e.g., P2) is cleaved from the antibody component after internalization, bound to class II MHC heterodimers, and transported to the cell surface. Cytotoxic T cells generated with the LL1-P2 vaccine will then recognize the HLA-II-peptide complex on the cellular membrane and destroy the tumor cell. This general approach can be used to treat other tumors that express the HLA-DR complex, or to treat autoimmune diseases that are caused by cells expressing the HLA-DR complex.

Immunoconjugates also can be used to induce or to boost the immune response to a tumor cell or to an infectious agent using a peptide that contains a suitable epitope. As an illustration, a peptide containing the A3B3 domain of CEA can be conjugated to IMMU-LL1 antibody (or fragment) and injected subcutaneously to establish primary sensitization against CEA, or injected intravenously to boost the immune response to CEA.

Similarly, immunoconjugates comprising CDRs of anti-idiotype antibodies can be used to induce or to boost the immune response. In this approach, a peptide containing the amino acid sequence of a CDR is conjugated with an antibody or antibody fragment. For example, the minimal recognition unit of IMMU-14 Ab2 antibody can be conjugated with IMMU-LL1 antibody or antibody fragment. The preparation of IMMU-14 anti-idiotype antibodies is described in Example 2.

According to preferred methods of immunotherapy, the immune response is further amplified by the administration of cytokines. Examples of cytokines include the interferons (INFs), interleukins (ILs) and tumor necrosis factors. INF-γ induces macrophages, as well as cell-surface class II histocompatibility antigens on lymphoid cells and monocytes. See, for example, Klegerman et al., "Lymphokines and Monokines," in BIOTECHNOLOGY AND PHARMACY, Pezzuto et al. (eds.), pages 53-70 (Chapman & Hall 1993), and Roitt et al., IMMUNOLOGY, 3rd Edition, pages 7.8-7.14 (Mosby 1993). IL-2 is a T cell growth factor and a stimulator of natural killer cells and tumor-reactive T cells. Id. Thus, INF-γ and IL-2 are preferred cytokines for the augmentation of the immune response.

IL-12 is another preferred cytokine for enhancing the immune response to the immunoconjugates of the present invention. This cytokine is produced by phagocytic cells in response to bacteria, bacterial products and intracellular parasites. See, for example, Trinchieri, *Annu. Rev. Immunol.* 13: 251 (1995). IL-12 induces cytokine production, primarily INF-γ, by natural killer cells and by T cells, and IL-12 acts as a growth factor for activated natural killer cells and T cells, enhances the cytotoxic activity of natural killer cells, and stimulates cytotoxic T cell generation. Id. In experimental animal model systems, IL-12 has been used to treat *Schistosoma mansoni, Mycobacterium avium, Histoplasma capsulatum*, as well as sarcoma, lung metastases. Wynn et al., *Nature* 376: 594 (1995); Castro et al., *J. Immunol.* 155: 2013 (1995); Zhou et al., *J. Immunol.* 155: 785 (1995); Zitvogel et al., *J. Immunol.* 155: 1393 (1995).

The antibodies and fragments of the present invention can be used as vaccines by conjugating the antibodies or fragments to a soluble immunogenic carrier protein. Suitable carrier proteins include keyhole lympet hemocyanin, which is the preferred carrier protein. The antibodies and fragments can be conjugated to the carrier protein using standard methods. See, for example, Hancock et al, "Synthesis of Peptides for Use as Immunogens," in METHODS IN MOLECULAR BIOLOGY: IMMUNOCHEMICAL PROTOCOLS, Manson (ed.), pages 23-32 (Humana Press 1992). Immunoconjugates comprising one of the above-described antigenic peptides do not require the addition of an immunogenic carrier protein.

A preferred vaccination composition comprises an antibody conjugate or fragment conjugate, and an adjuvant. Examples of suitable adjuvants include aluminum hydroxide and lipid. Methods of formulating vaccine compositions are well-known to those of ordinary skill in the art. See, for example, Rola, "Immunizing Agents and Diagnostic Skin Antigens," in REMINGTON'S PHARMACEUTICAL SCIENCES, 18th Edition, Gennaro (ed.), pages 1389-1404 (Mack Publishing Company 1990).

Additional pharmaceutical methods may be employed to control the duration of action of a vaccine in a therapeutic application. Control release preparations can be prepared through the use of polymers to complex or adsorb the immunoconjugates, antibodies or fragments. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release of an immunoconjugate, antibody or antibody fragment from such a matrix depends upon the molecular weight of the immunoconjugate, antibody or antibody fragment, the amount of immunoconjugate, antibody or antibody fragment within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990).

The therapeutic preparations of the present invention can be formulated according to known methods to prepare pharmaceutically useful compositions, whereby immunoconjugates, antibodies or antibody fragments are combined in a mixture with a pharmaceutically acceptable carrier. A composition is said to be a "pharmaceutically acceptable carrier" if its administration can be tolerated by a recipient mammal. Sterile phosphate-buffered saline is one example of a pharmaceutically acceptable carrier. Other suitable carriers are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990).

The immunoconjugates, antibodies or fragments may be administered to a mammal intravenously or subcutaneously. Moreover, the administration may be by continuous infusion or by single or multiple boluses. Preferably, an antibody vaccine is administered subcutaneously, while an antibody preparation that is not a vaccine is administered intravenously. In general, the dosage of administered immunoconjugates, antibodies or fragments for humans will vary depending upon such factors as the patient's age, weight, height, sex, general medical condition and previous medical history. Typically, it is desirable to provide the recipient with a dosage of immunoconjugates, antibodies or fragments which is in the range of from about 1 pg/kg to 10 mg/kg (amount of agent/body weight of patient), although a lower or higher dosage also may be administered as circumstances dictate.

For purposes of therapy, immunoconjugates, antibodies or fragments are administered to a mammal in a therapeutically effective amount. An antibody preparation is said to be administered in a "therapeutically effective amount" if the amount administered is physiologically significant. An agent is physiologically significant if its presence results in a detectable change in the physiology of a recipient mammal. In particular, an antibody preparation of the present invention is physiologically significant if its presence invokes a humoral and/or cellular immune response in the recipient mammal.

A cytokine, such as INF-γ, IL-2, or IL-12 may be administered before and during the administration of an Ab1 vaccine or an Ab2 vaccine. Alternatively, cytokines may be administered together before and during the administration of an antibody vaccine. Cytokines are administered to the mammal intravenously, intramuscularly or subcutaneously. For example, recombinant IL-2 may be administered intravenously as a bolus at $6\times10^5$ IU/kg or as a continuous infusion at a dose of $18\times10^6$ IU/m$^2$/d. Weiss et al., *J. Clin. Oncol.* 10: 275 (1992). Alternatively, recombinant IL-2 may be administered subcutaneously at a dose of $12\times10^6$ IU. Vogelzang et al., *J. Clin. Oncol.* 11: 1809 (1993). Moreover, INF-γ may be administered subcutaneously at a dose of $1.5\times10^6$ U. Lienard et al., *J. Clin. Oncol.* 10: 52 (1992). Furthermore, Nadeau et al., *J. Pharmacol. Exp. Ther.* 2.74: 78 (1995), have shown that a single intravenous dose of recombinant IL-12 (42.5 μg/kilogram) elevated IFN-γ levels in rhesus monkeys.

Suitable IL-2 formulations include PROLEUKIN (Chiron Corp./Cetus Oncology Corp.; Emeryville, Calif.) and TECELEUKIN (Hoffman-La Roche, Inc.; Nutley, N.J.). ACTIMMUNE (Genentech, Inc.; South San Francisco, Calif.) is a suitable INF-γ preparation.

In addition, bispecific antibodies may be administered after the initial Ab1 treatment. The function of the bispecific antibodies is to bridge lymphocytes with CEA-bearing tumor cells and to trigger the lymphocyte-mediated cytolysis. Bispecific antibodies can be administered according to above-described general guidelines. However, bispecific antibodies, unlike antibody vaccines, are not conjugated with immunogens.

Those of ordinary skill in the art will appreciate that the above-described methods can be used to provide prophylaxis against infectious agents. Thus, the present invention contemplates the use of methods described herein to provide protection to a mammal before exposure to an infectious agent.

The present invention, thus generally described, will be understood more readily by reference to the following examples, which are provided by way of illustration and are not intended to be limiting of the present invention.

EXAMPLE 1

Production of Murine Anti-CEA MAb (MN-14)

The production of MN-14, a Class III, anti-CEA MAb, has been described by Hansen et al., *Cancer* 71: 3478 (1993), which is incorporated by reference. Briefly, a 20 gram BALB/c female mouse was immunized subcutaneously with 7.5 μg of partially-purified CEA in complete Freund adjuvant. On day 3, the mouse was boosted subcutaneously with 7.5 μg of CEA in incomplete Freund adjuvant and then, the mouse was boosted intravenously with 7.5 μg of CEA in saline on days 6 and 9. On day 278, the mouse was given 65 μg of CEA intravenously in saline and 90 μg of CEA in saline on day 404. On day 407, the mouse was sacrificed, a cell suspension of the spleen was prepared, the spleen cells were fused with murine myeloma cells, SP2/0-Ag 14 (ATCC CRL 1581) using polyethylene glycol, and the cells were cultured in medium containing 8-azaguanine. Hybridoma supernatants were screened for CEA-reactive antibody using an $^{125}$I-CEA radioimmunoassay (Roche; Nutley, N.J.). Positive clones were recloned.

One clone, designated MN-14, had properties similar to the Class III anti-CEA-specific MAb, NP-4, being unreactive with normal cross-reactive antigen and meconium antigen. However, MN-14, compared with NP-4, demonstrated significantly superior tumor targeting in a human colon tumor xenograft model and consistently stronger staining of frozen sections of colon cancer.

EXAMPLE 2

Preparation of CDR-Grafted MN-14 (hMN-14) and hAb1 Vaccine (hMN-14 Vaccine)

A modified antibody was prepared in which the complementarity determining regions (CDR) of MN-14 were engrafted to the framework regions of human IgG$_1$ antibody. The CDR-grafted ("humanized") MN-14 antibody was designated "hMN-14." General techniques for producing humanized antibodies are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993).

To prepare hMN-14 vaccine, hMN-14 was conjugated with keyhole lympet hemocyanin. Typically, patients are immunized with subcutaneous injections of the conjugate (2 mg/injection) mixed with 100 μl ($10^7$ organisms) of Tice *Bacillus Calmette*-Guérin (Organon; West Orange, N.J.).

EXAMPLE 3

Preparation of Rat Monoclonal Ab2 to MN-14 (WI2) and Ab2 Vaccine (WI2 Vaccine)

Rat Ab2 to MN-14 was prepared as described by Losman et al., *Int. J. Cancer* 56: 580 (1994), which is incorporated by reference. Briefly, female 3-week-old Copenhagen rats were injected intraperitoneally with 200 μg of MN-14 F(ab')$_2$ fragments emulsified in Freund's complete adjuvant. Animals were boosted at days 200, 230, and 235 with the same amount of antigen in Freund's incomplete adjuvant. Four days after the last injection, animals were sacrificed, spleen cell suspensions were prepared, and the cells were fused with murine non-secreting plasmocytoma SP2/0 using standard techniques. Hybridoma cells were cultured in the presence of rat peritoneal feeder cells (10,000 cells/200 μl culture well).

Culture supernatants were screened by ELISA for reactivity with MN-14 and absence of reactivity with control murine MAbs. Positive hybridomas were cloned at least twice by limiting dilution in the presence of rat peritoneal feeder cells.

WI2 is an $IgG_{1k}$ Ab2 which is specific for MN-14 and does not react with other isotype-matched anti-CEA MABs. Immunization of mice or rabbits with WI2 (but not with control rat IgG) induced the production of Ab1' anti-CEA antibodies. Thus, WI2 can be used as an idiotype vaccine for patients with CEA-producing tumors.

WI2 vaccine is prepared from WI2 as described for the preparation of hMN-14 vaccine.

EXAMPLE 4

Treatment with hMN-14 Vaccine (hAb1-Vaccine) and WI2 Vaccine (Ab2 Vaccine)

A patient with Dukes C colon carcinoma underwent a primary tumor resection for cure and then, was placed on fluorouracil and Levamisole adjuvant therapy. The pre-operative CEA titer was 15.5 ng/ml. Three months after primary surgery, the CEA titer was in the normal range, that is, below 2.5 ng/ml.

Two years later, the patient was found to have a CEA titer of 25 ng/ml and a CAT scan showed a 5 cm tumor in the left lobe of liver and a 2 cm tumor in the right lobe. One month later, the CEA titer was 25 ng/ml and the patient was immunized subcutaneously with 2 mg of hAb1 vaccine (day 0). Immunization was repeated at day 7.

On day 30, the patient was found to have lymphocytes reactive with the Ab1 (T2 cells). On day 40, the patient was given 100 mg of the hAb1 intravenously. Two months later, the CEA titer was 5 ng/ml and a CAT scan showed that the left lobe tumor had decreased to 2 cm in size, while the right lobe tumor had completely regressed.

Six months later, the left lobe tumor had increased in size, and a large tumor mass was found in the abdomen, as confirmed by needle biopsy. The CEA titer had increased to 50 ng/ml. The patient was given the WI2 Ab2 vaccine (2 mg) subcutaneously on day 0 and on day 30. A severe reaction occurred at the injection site on day 35, which slowly resolved.

Three months later, the CEA titer was found to be less than 2.5 ng/ml, and the left lobe tumor had completely resolved. The mass in the abdomen was reduced in size and a needle biopsy failed to reveal the presence of a tumor, demonstrating only fibrous tissue infiltrated with lymphocytes.

Two years later, a CAT scan showed that tumor recurrence had not occurred, and the CEA titer was less than 2.5 ng/ml.

EXAMPLE 5

Preparation and Use of an Immunoconjugate to Induce Primary Sensitization

IMMU-LL1 (EPB-1) is a murine monoclonal antibody that binds with the HLA-DR complex on the plasma membrane of macrophages, monocytes, and B-lymphocytes and then, rapidly internalizes. The preparation of IMMU-LL1 is described by Palak-Byczkowska et al., Cancer Res. 49: 4568 (1989). F(ab')$_2$ fragments are prepared from intact IMMU-LL1 by conventional proteolysis techniques, and conjugated with the P2 peptide [SEQ ID NO: 1] of tetanus toxin at the hinge region, as described above. Alternatively, the P2 peptide is conjugated via an engineered carbohydrate moiety on the light chain of the antibody fragments using the techniques of Leung et al., J. Immunol. 154: 5919-(1995).

The IMMU-LL1-P>2 vaccine is administered subcutaneously to establish primary sensitization due to the strong MHC-restricted immune response induced by the P2 moiety. The IMMU-LL1-P2 vaccine also can be administered intravenously to boost the immune response.

LL2 is a murine monoclonal antibody that binds with CD22 on B-cell lymphomas. See, for example, Goldenberg et al., J. Clin. Oncol. 9: 548 (1991); Murthy et al., Eur. J. Nucl. Med. 19: 394 (1992). Humanized LL2 is prepared as described by Leung et al., Hybridoma 13:469 (1994), and antibody fragments of humanized LL2 are prepared using standard techniques. An LL2-P2 conjugate is prepared as described above and administered intravenously to the sensitized subject to direct the immune response against tumor cells bearing the CD22 antigen.

EXAMPLE 6

Preparation and Use of an Immunoconjugate Comprising an Epitope of a Tumor Associated Antigen To target CEA-expressing tumor cells, the A3B3 epitope of CEA is produced recombinantly or by peptide synthesis using the known amino acid sequence. Jessup et al., Int. J. Cancer 55: 262 (1993); Zhou et al., Cancer Res. 53: 3817 (1993); and Hefta et al., Cancer Res. 52: 5647 (1992). A3B3 peptides are conjugated to IMMU-LL1 antibody or fragment using standard techniques described above. The IMMU-LL1-A3B3 vaccine is administered subcutaneously to induce the immune response against CEA-bearing tumor cells. The vaccine also can be administered intravenously to boost the immune response against such tumor cells.

EXAMPLE 7

Preparation and Use of an Immunoconjugate Comprising a Minimal Recognition Unit

Peptides having the amino acid sequence of minimal recognition units of the Ab2 antibody described in Example 2 are prepared using the techniques described in section 6 above. The peptides are conjugated with IMMU-LL1 antibodies or fragments to produce immunoconjugates that are suitable for inducing (via subcutaneous administration) or boosting (via intravenous administration) the immune response.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

---

What is claimed is:

1. A vaccine comprising an immunoconjugate that comprises:
    a) an antibody component that binds with the invariant chain (Ii) of the HLA-DR complex on a cell expressing said HLA-DR complex and is rapidly internalized into said cell; and
    b) an antigenic peptide comprising at least one epitope of a TAA (tumor-associated antigen),
wherein administration of said vaccine to a subject induces humoral and cellular immune responses against a tumor that expresses the TAA.

2. The vaccine of claim 1, further comprising at least one cytokine selected from the group consisting of interferon-α, interferon-β, interferon-γ, interleukin-2 and interleukin-12.

3. The vaccine of claim 2, further comprising interferon-γ, interleukin-2 and interleukin-12.

4. The vaccine of claim 1, wherein the TAA is carcinoembryonic antigen (CEA).

5. The vaccine of claim 4, wherein the epitope is an epitope of A3B3.

6. The vaccine of claim 1, wherein the TAA is alpha-fetoprotein (AFP).

7. The vaccine of claim 1, wherein the TAA is human chorionic gonadotrophin-beta (HCG-β).

8. The vaccine of claim 1, wherein the TAA is prostatic acid phosphatase (PAP).

9. A vaccine comprising an immunoconjugate that comprises:
    a) an antibody component that binds with the invariant chain (Ii) of the HLA-DR complex on a cell expressing said HLA-DR complex and is rapidly internalized into said cell; and
    b) an anti-idiotypic antibody or fragment thereof that mimics an epitope of a TAA;
wherein administration of said vaccine to a subject induces humoral and cellular immune responses against a tumor that expresses the TAA.

10. The vaccine according to claim 9, wherein the anti-idiotypic antibody mimics an epitope of CEA.

11. The vaccine according to claim 9, wherein the anti-idiotypic antibody mimics an epitope of A3B3.

12. The vaccine of claim 9, wherein the anti-idiotypic antibody mimics an epitope of alpha-fetoprotein (AFP).

13. The vaccine according to claim 9, wherein the anti-idiotypic antibody mimics an epitope of HCG-β.

14. The vaccine according to claim 9, wherein the anti-idiotypic antibody mimics an epitope of PAP.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 16 amino acids
      (B) TYPE: amino acid
      (C) STRANDEDNESS: single
      (D) TOPOLOGY: linear (xi) SEQUENCE DESCRIPTION: SEQ ID NO: 1:

Cys Gln Tyr Ile Lys Ala Asn Ser Lys Phe Ile Gly Ile Thr Glu Leu
1          5                   10               15

(2) INFORMATION FOR SEQ ID NO: 2:

(i) SEQUENCE CHARACTERISTICS:
      (A) LENGTH: 22 amino acids
      (B) TYPE: amino acid
      (C) STRANDEDNESS: single
      (D) TOPOLOGY: linear (xi) SEQUENCE DESCRIPTION: SEQ ID NO: 2:

Phe Asn Asn Phe Thr Val Ser Phe Trp Leu Arg Val Pro Lys Val Ser
1          5                   10               15

Ala Ser His Leu Glu Cys
            20